(12) United States Patent
Foster et al.

(10) Patent No.: US 8,731,664 B2
(45) Date of Patent: May 20, 2014

(54) REDUCED DIAMETER AXIAL ROTARY PUMP FOR CARDIAC ASSIST

(75) Inventors: Graham Foster, Swansea (GB); Kevin Fernquest, Neath (GB)

(73) Assignee: Calon Cardio Technology Limited, Swansea (GB)

( * ) Notice: Subject to any disclaimer, the term of this patent is extended or adjusted under 35 U.S.C. 154(b) by 1027 days.

(21) Appl. No.: 12/664,163

(22) PCT Filed: Jun. 12, 2008

(86) PCT No.: PCT/GB2008/050439
§ 371 (c)(1),
(2), (4) Date: Dec. 11, 2009

(87) PCT Pub. No.: WO2008/152425
PCT Pub. Date: Dec. 18, 2008

(65) Prior Publication Data
US 2010/0174131 A1 Jul. 8, 2010

(30) Foreign Application Priority Data

Jun. 14, 2007 (GB) .................................. 0711479.6
Jun. 15, 2007 (GB) .................................. 0711598.3

(51) Int. Cl.
*A61N 1/00* (2006.01)
(52) U.S. Cl.
USPC .......................................................... 607/16
(58) Field of Classification Search
USPC ...................................... 600/16–18; 623/3.13
See application file for complete search history.

(56) References Cited

U.S. PATENT DOCUMENTS

| 4,846,152 | A | * | 7/1989 | Wampler et al. ................. 600/16 |
| 5,205,721 | A | * | 4/1993 | Isaacson ........................ 417/356 |
| 5,443,503 | A | * | 8/1995 | Yamane ........................ 623/3.14 |
| 5,851,174 | A | * | 12/1998 | Jarvik et al. .................... 600/16 |
| 5,911,685 | A | * | 6/1999 | Siess et al. ...................... 600/16 |
| 6,042,347 | A | | 3/2000 | Scholl et al. |
| 6,053,705 | A | | 4/2000 | Schob et al. |
| 6,176,822 | B1 | * | 1/2001 | Nix et al. ........................ 600/17 |
| 6,190,319 | B1 | * | 2/2001 | Goldowsky .................... 600/437 |
| 6,422,990 | B1 | | 7/2002 | Prem |
| 6,436,027 | B1 | * | 8/2002 | Goldowsky ..................... 600/16 |
| 7,011,620 | B1 | * | 3/2006 | Siess ............................... 600/16 |
| 2012/0088954 | A1 | * | 4/2012 | Foster ............................. 600/16 |

FOREIGN PATENT DOCUMENTS

| EP | 1738783 A1 | 12/2009 |
| WO | 2005032620 A1 | 4/2005 |
| WO | 2007003351 A1 | 1/2007 |

* cited by examiner

*Primary Examiner* — Christopher D Koharski
*Assistant Examiner* — Roland Dinga
(74) *Attorney, Agent, or Firm* — Larson & Anderson, LLC

(57) ABSTRACT

The pump is of an axial flow rotary type suitable for implantation into the human heart or vascular system. The pump has an elongate tubular casing (1) including an electric motor (4) and defining an inlet (2) for blood, an outlet (3) for blood longitudinally spaced from the inlet and a substantially axial blood flow path (8) from the inlet to the outlet. An elongate rotatable element (7) is arranged to fit within the casing with spacing (15) between an outer surface of the rotatable element and an inner surface of the casing; the rotatable element comprises an electric motor rotor portion (10) arranged to be driven by the electric motor stator and a primary substantially axial blood flow path along the inside of the rotatable element. A rotary impeller (11) is provided axially spaced from the rotor portion for impelling blood along the primary flow path.

21 Claims, 9 Drawing Sheets

REDUCED DIAMETER AXIAL ROTARY PUMP FOR CARDIAC ASSIST

The present invention concerns miniaturised pumps suitable for implantation into the human heart or vascular system Heart Failure is major global health problem resulting in many thousands of deaths each year. Until recently the only way to curatively treat advanced stage heart failure has been by heart transplant or the implantation of a total mechanical heart. Unfortunately donor hearts are only able to meet a tiny fraction of the demand and total mechanical hearts have yet to gain widespread acceptance due to the technical difficulties involved with these devices.

Ventricle assist devices (VADs) have been gaining increased acceptance over the last three decades primarily as a bridge to transplant devices. The devices are implanted long term and work alongside a diseased heart to boost its output and keep the patient alive and/or give a better quality of life whilst awaiting transplant. The use of these devices has had an unexpected result in some patients: the reduction in strain on the heart over a period of time has led to significant spontaneous recovery of the left ventricle. This gives hope to many patients for whom a donor heart may not become available as it could be the case that the early implantation of a VAD may allow their condition to recover before the disease reaches the most advanced stages. It is also a far more preferable outcome to have ones own heart recover than undergo a transplant even if donor hearts are available.

At present, the main reason preventing VADs from being fitted on a more routine basis is the highly invasive surgical procedure required to fit the devices. Typically a sternotomy, full heart lung bypass, and major procedures to the heart and thoracic aorta are required to fit a VAD. Presently the expense and risk of such an operation cannot be justified except in the case of those in the most advanced stages of Heart Failure. If the long term implantation of a VAD or an equivalent circulatory assist device (CAD) could be achieved with a less invasive surgical procedure, ideally eliminating the need for a sternotomy and heart lung bypass, then the use of CADs to treat heart failure in its earlier stages could become far more widespread and routine.

The key to a less invasive implantation procedure for a CAD is to make the device as small as possible so that it can be implanted using a 'keyhole' type procedure. There are currently available devices for short term use only (maximum two weeks) that are intended for use as a bridge to recovery. These short term devices are implanted into the heart via the femoral artery using a simple catheter delivery procedure which results in a very low level of patient trauma. If a long term implantable CAD could be developed that is able to be inserted in a similar way to short term CADs, then the vision of routinely using CADs to treat earlier stage heart failure would be a significant step closer.

As a result of the above considerations, there exists a need to develop miniaturised cardiac pumps suitable for implantation into the human heart or vascular system. Furthermore the emphasis on the miniaturisation should be to decrease the diameter of the pump even if this decrease comes at the expense of a slight increase in length. A keyhole type surgical procedure will always suit devices of a more elongate shape, and this is particularly true of devices that are catheter delivered through a peripheral artery.

According to the invention therefore, there is provided a pump suitable for implantation into the human heart or vascular system, the pump being an axial flow rotary pump having an elongate tubular casing including an electric motor stator and defining an inlet for blood, an outlet for blood longitudinally spaced from the inlet and a substantially axial blood flow path from the inlet to the outlet.

The pump includes an elongate rotatable element arranged to fit within the casing with spacing between an outer surface of the rotatable element and an inner surface of the casing, the rotatable element comprising an electric motor rotor portion arranged to be driven by said electric motor stator and a primary substantially axial blood flow path along the inside of the rotatable element, and a rotary impeller axially spaced from said rotor portion for impelling blood along said primary flow path.

The casing preferably has a substantially uniform outer diameter along at least the majority of the length thereof.

It is further preferred that at least part of the rotatable element forming the primary blood flow path has a substantially uniform inner diameter along at least the majority of its length; it is sometimes preferred that the rotatable element is tubular.

In a further preferred feature, the impeller is disposed in a pumping chamber having an internal diameter greater than the outer diameter of the rotatable element, such as greater than the inner diameter of the rotatable element.

Generally, the pump includes a secondary blood flow path. In some embodiments it is preferred that a secondary blood flow path is defined in spacing between an outer surface of the rotatable element and an inner surface of the casing (although secondary blood flow paths in other locations are also envisaged as will be explained below). Such a flow path in spacing between the outer surface of the rotatable element and the inner surface of the casing serves to suspend the rotor in blood and prevent the inner rotating element from contacting the outer casing. Centering forces may be provided by hydrodynamic bearings and/or magnetic bearings.

in some further embodiments of the invention, as will be described with reference to some of the embodiments illustrated in the accompanying drawings, a generally central bore may be provided in the rotatable element to serve as a secondary blood flow path.

In some embodiments, at least one of the outer surface of the rotatable element and the inner surface of the casing preferably has at least one longitudinally or helically extending groove or rib. Such a groove or rib typically extends helically and continuously around the rotatable element, typically to provide a combined hydrodynamic bearing and pumping effect. The rib may have a slipper pad profile when viewed in section.

In some embodiments (namely where the inlet is at one end of the casing and the outlet is at the other end), the pump may be described as a 'straight though' type design having an inlet at one end and an outlet at the other end thereof. In such embodiments, the rotatable element may be tubular.

In other embodiments, at least one of the inlet and the outlet comprises at least one aperture provided in a wall of the casing and the other thereof being an open end thereof. The pump according to the latter embodiment may be described as an axial flow rotary pump of a 'side inlet or outlet' type design having an inlet at one end and an outlet in the side of the outer casing or vice versa. In such embodiments the end remote from the open end is generally closed.

It is further sometimes desirable to include a stator element which serves to retain the rotatable element (as will be described in more detail by way of reference to the respective embodiments illustrated in FIGS. 5 and 6, FIGS. 11 to 14 and FIGS. 15 to 18 of the accompanying drawings). Such stator elements can further provide improved efficiency, as will be explained below with reference to the embodiments mentioned.

The pump is electric motor driven and preferably utilises an embedded brushless DC motor. The pump is desirably of a contactless design employing hydrodynamic and/or magnetic forces to suspend the rotating part in the blood and is therefore near wearless in operation making it suitable for long term use.

A fixed outer casing may define the inlet and outlet and also houses motor stator components. Within the outer casing is an inner rotatable element that defines a primary blood flow path along a central axis of the casing; the rotatable element comprises a motor rotor portion and a pumping chamber with impeller. The motor rotor portion is positioned such that it can co-operate with a motor stator in the casing.

In contrast to other designs of axial flow blood pumps with a central blood flow path, the motor rotor portion and the pumping chamber are axially offset. This axial offset allows the overall diameter of the pump to be reduced whilst maintaining efficiency and throughput. For a similar throughput there may be a small increase in pump length but given the pumps intended use this is of less importance than the reduction in diameter.

The motor typically is of a brushless DC design employing electronic commutation for speed control. It should be noted however that motors of this type are well known and for this reason the conventional motor components shown in the accompanying representations are schematic representations only.

Embodiments of the invention and preferred features thereof will now be described in more detail, with reference to accompanying drawings, in which.

Referring first to the embodiment of FIGS. 1 to 4, in which like parts are denoted by like reference numerals, there is shown a miniature axial flow electric motor driven rotary cardiac pump, comprising a fixed tubular outer casing 1 defining an inlet 2 at one end and an outlet 3 at the other. It is desirable in this embodiment that the outer casing should be of a uniform outer diameter, in order to allow easy insertion into an artery or specific delivery device.

Integral with the outer casing 1 is a motor stator 4; the latter houses stator windings 5 and a back iron 6. Rotatably held within the casing is a tubular rotatable element 7 that defines a primary blood flow path 8 through its central bore. The tubular rotatable element 7 also includes a pumping chamber 9 and a motor rotor portion 10. The pumping chamber includes an impellor 11 and a series of impellor blades 12.

The tubular pumping chamber 9 is such that the impellor 11 is shrouded, which substantially eliminates the high shear stress regions that might otherwise exist between impellor tips and a containing tube in non-shrouded designs. The reduction of shear stresses in a blood pump is particularly important, because high shear stresses can lead to haemolysis; features that reduce shear stress are therefore particularly advantageous.

The motor rotor portion further comprises rotor permanent magnets 13 which are positioned to be able to co-operate with the motor stator 4. An axial offset 14 of the pumping chamber 9 and motor rotor portion allows, for any given outer diameter, the size of the both impellor and the motor components to be increased over that which would be possible if these components were to be axially aligned; as a result the throughput of the pump can be increased correspondingly. Similarly a pump of a given throughput could have its diameter reduced by adopting this axial offset arrangement.

A clearance between the inner tubular rotatable element 7 and the outer casing 1 defines a secondary blood flow path 15 which allows the inner rotatable element 7 to be completely blood suspended; this feature therefore allows the pump to be near wearless in operation. The inlet 16 for the secondary blood flow path is at the end of inner tubular rotatable element 7 which is downstream of the impellor 11 on the high pressure side of the pump. The outlet 17 is on the opposite side of the inner tubular rotatable element 7 in the low pressure zone of the pump which is upstream of the impellor 11.

Thus the secondary blood flow path will naturally flow from a high to low pressure. However, in the embodiment of FIGS. 1 to 4, the secondary blood flow is augmented by helical ribs 18 that serve the dual functions both of an additional pumping means for the secondary flow and of radial hydrodynamic bearings. The additional pumping means is achieved by the helixes giving an Archimedes screw pumping effect; this ensures that the flow rate in the secondary path helps to avoid risk of thrombus formation.

A hydrodynamic bearing is provided by the helical ribs 18 having a radial slipper pad bearing profile when viewed in section 19. The large area covered by the helical ribs 18 ensures that the centralising loads are well distributed over the rotating element, minimising shear stress at any one point and therefore minimising risk of haemolysis. In order to resist the axial thrust load imparted onto the tubular rotatable element 7 by the impellor 11, a flange with inclined slipper pad bearing 20 is provided. There is also provided a second opposing inclined slipper pad bearing 21. Even though this bearing 21 acts in the same direction of the axial thrust of the impellor 11, it will give improved overall system stability and provide resistance to shock loadings.

Both hydrodynamic bearings can be augmented by magnetic bearings 22 in order to provide a greater centralising force, particularly to resist external shock loadings.

In general, the whole of the pump is designed to provide a smooth, low shear stress blood passage in order to reduce the likelihood of haemolysis, without areas in which the flow could stagnate and give a risk of thrombosis.

A second embodiment of the invention will now be described with reference to FIGS. 5 and 6. The second embodiment works in a very similar way to that illustrated in FIGS. 1 to 4 and has most features in common with that first embodiment; accordingly the embodiment of FIGS. 5 and 6 will described by way of the differences between relative to the first embodiment.

Figure 1:
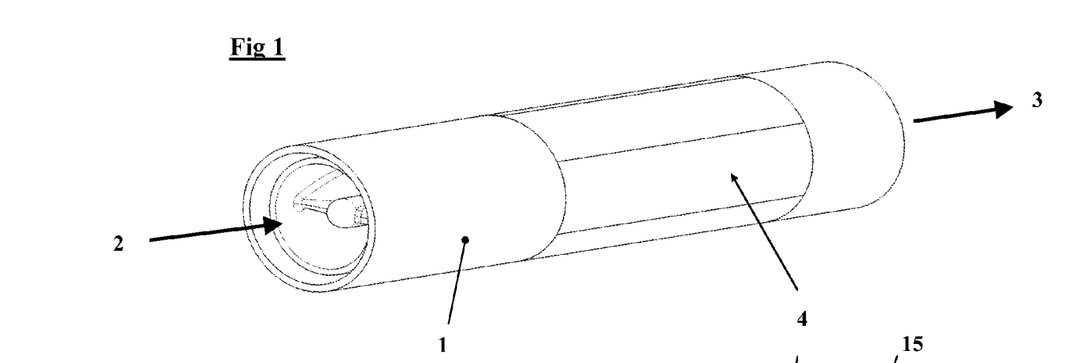
FIG. 1 is a perspective view of a first embodiment of a pump according to the invention.
Figure 2:
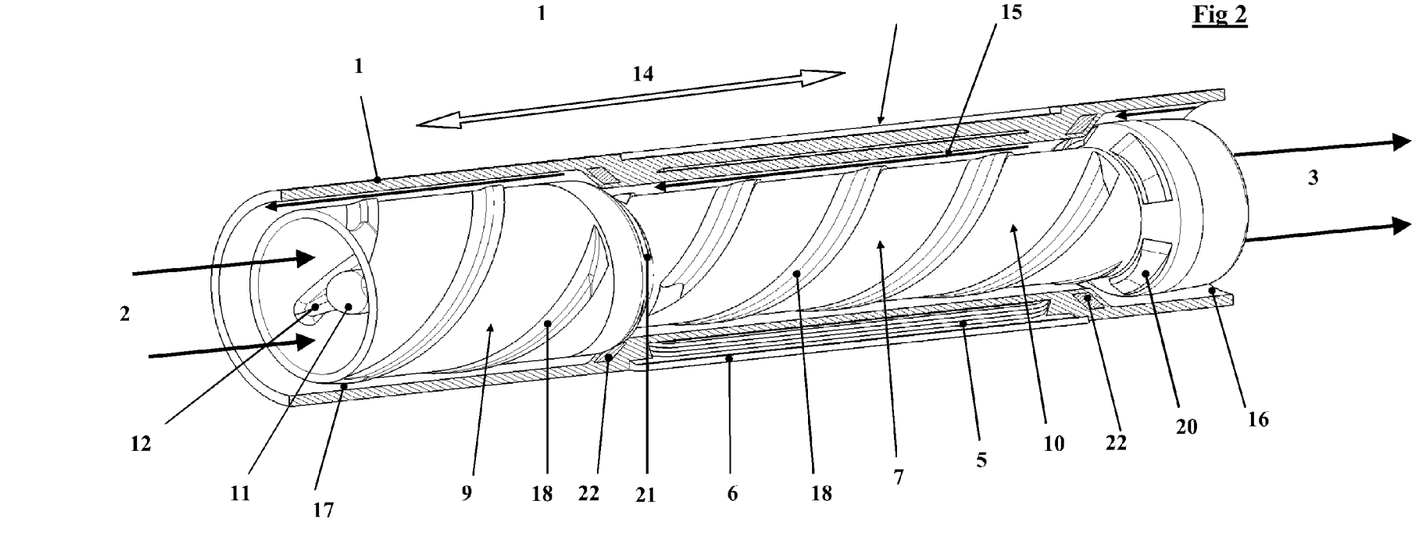
FIG. 2 is a partial cutaway view of the pump of FIG. 1.
Figure 3:
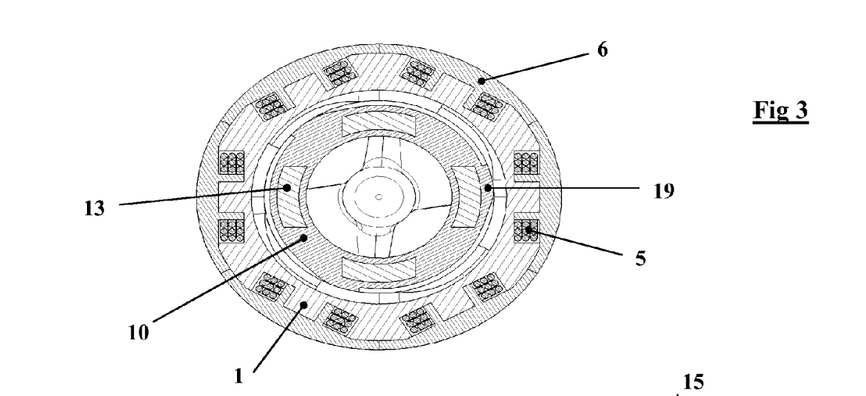
FIG. 3 is a full radial sectional view of the pump of FIG. 1.
Figure 4:
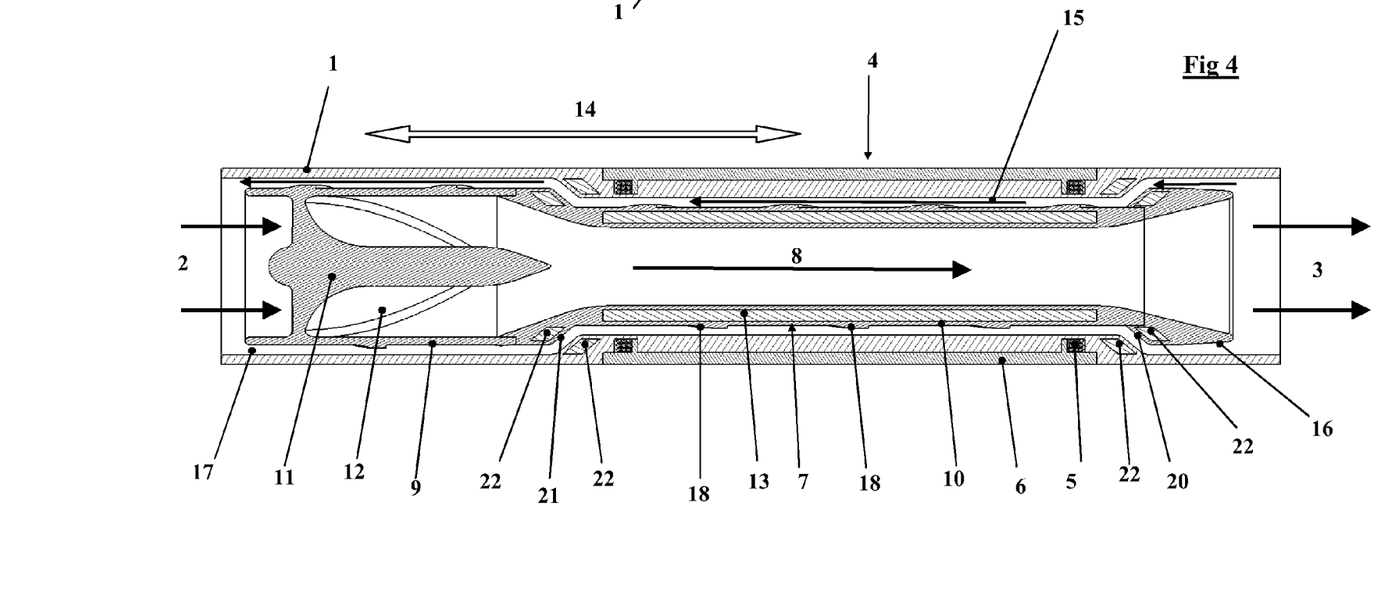
FIG. 4 is a full axial sectional view of a the pump of FIG. 1.
Figures 5, 6:
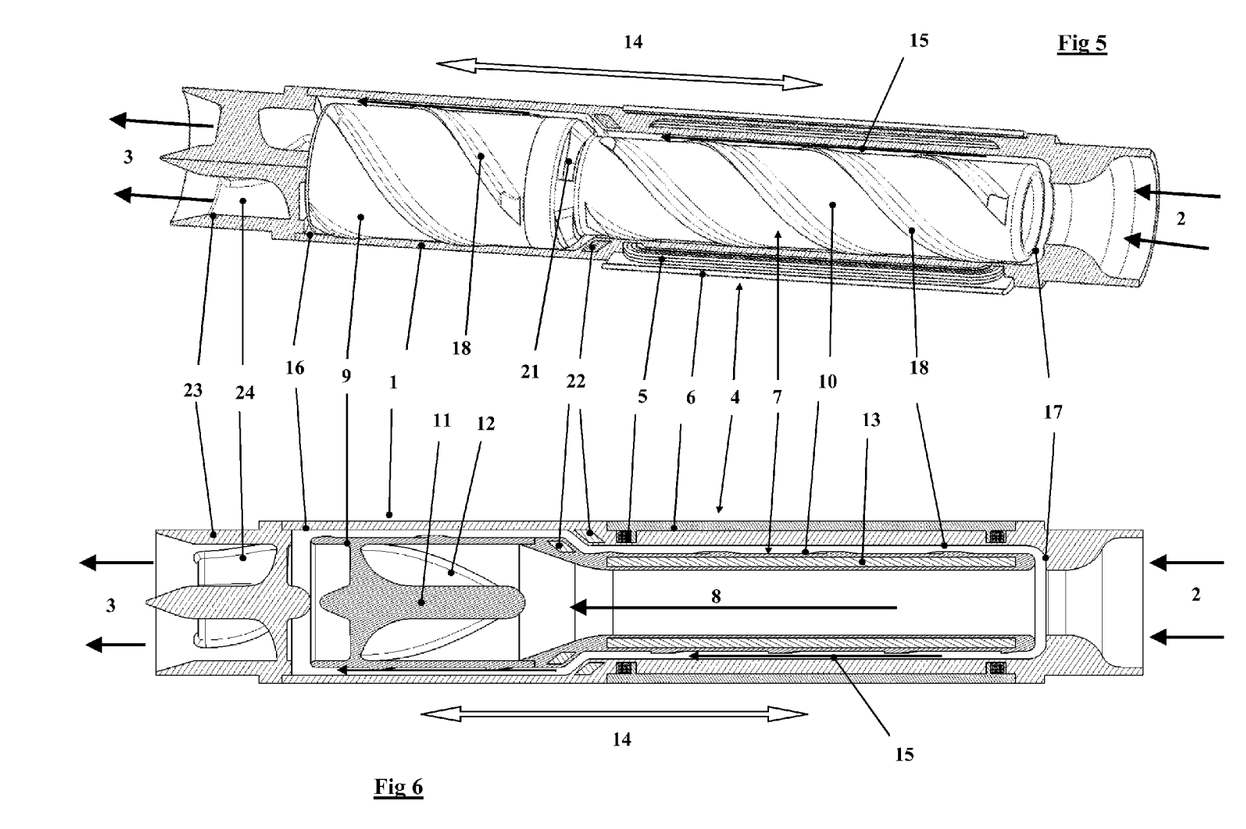
FIG. 5 is a partially cutaway view of a second embodiment of a pump according to the invention.
FIG. 6 is a full axial sectional view of the pump of FIG. 5.
Figure 7:
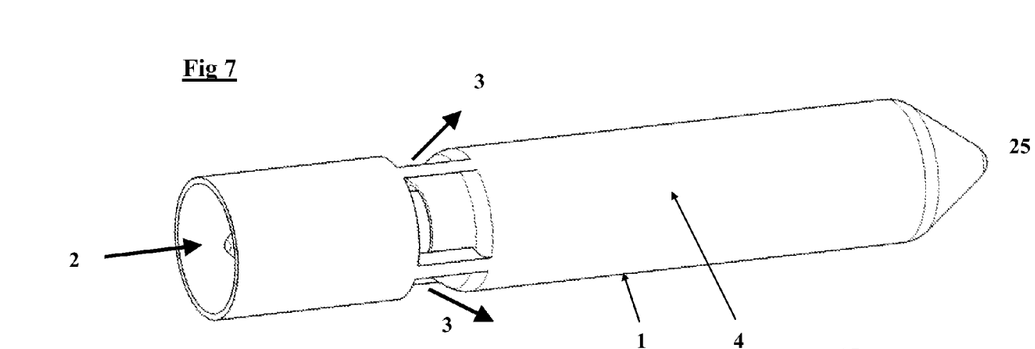
FIG. 7 is a perspective view of a third embodiment of a pump according to the invention.
Figure 8:
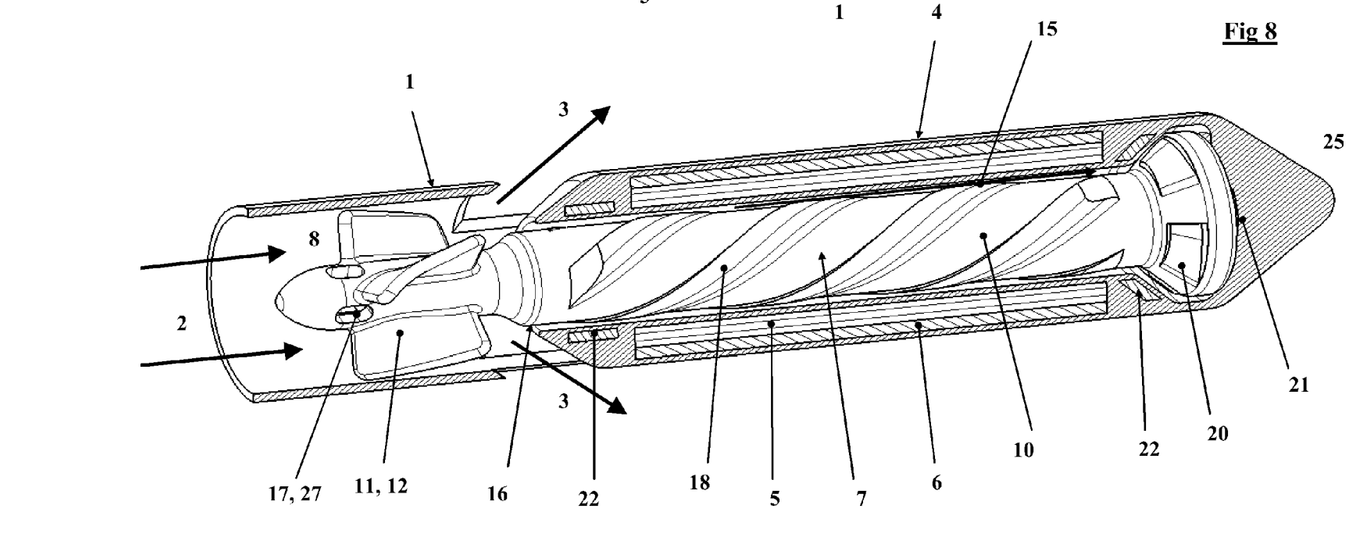
FIG. 8 is a partial cutaway view of the pump of FIG. 7.
Figure 9:
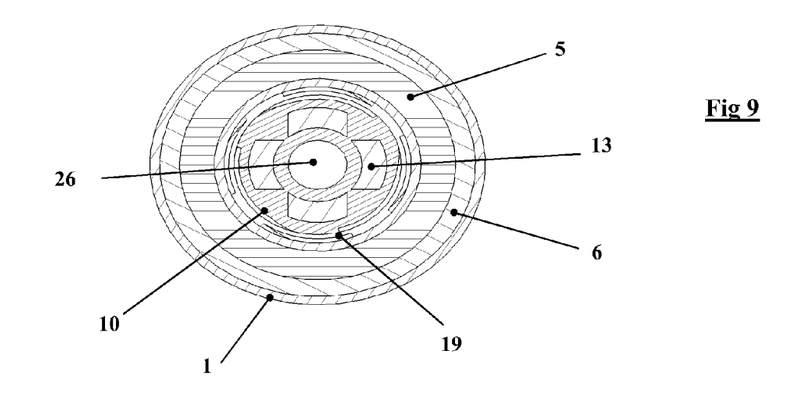
FIG. 9 is a full radial sectional view of the pump of FIG. 7.
Figure 10:
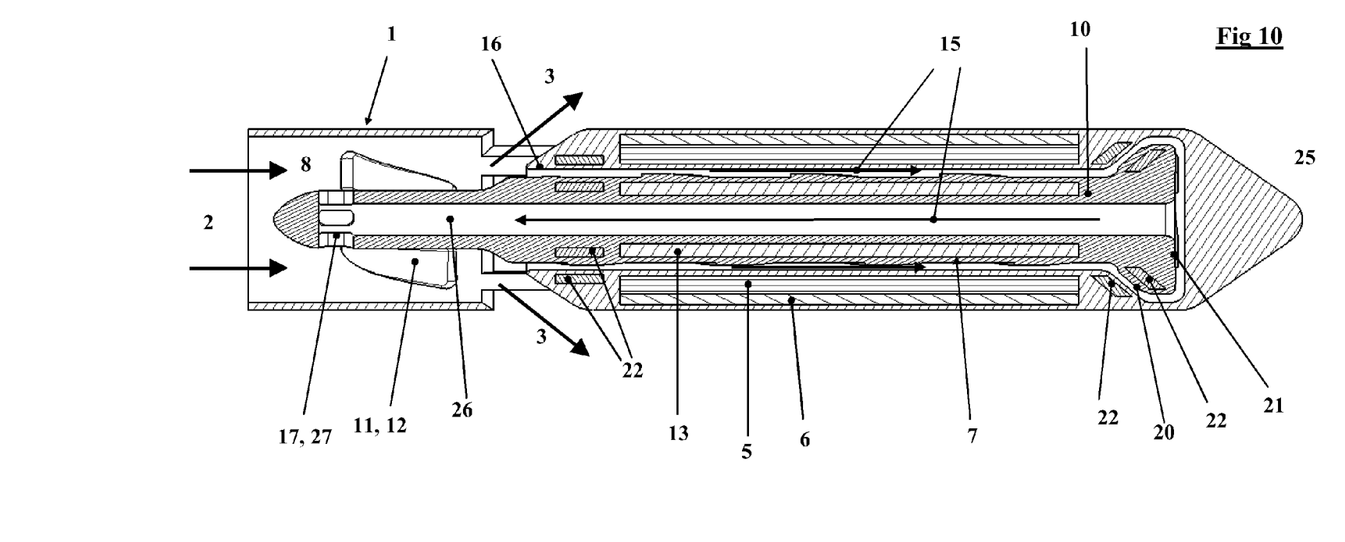
FIG. 10 is a full axial sectional view of the pump of FIG. 7.
Figure 11:
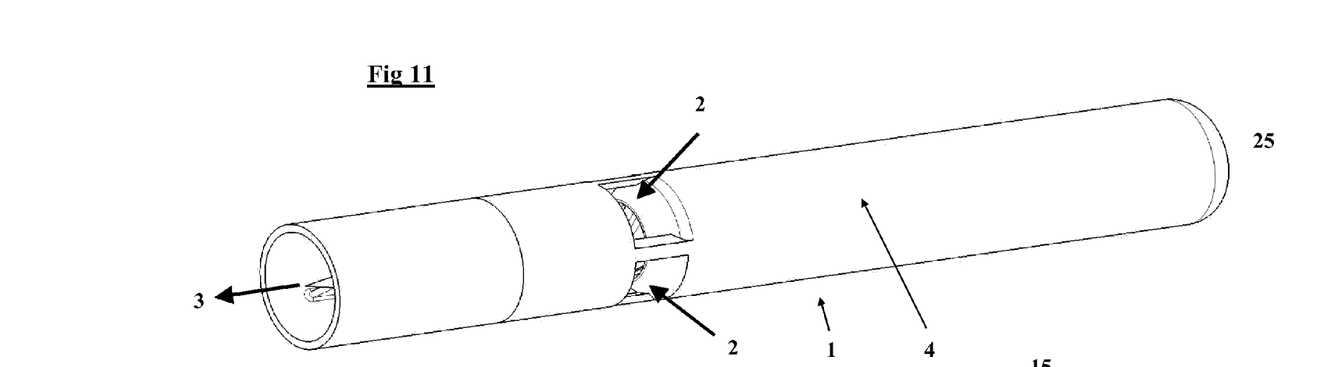
FIG. 11 is a perspective view of a fourth embodiment of a pump according to the invention.
Figure 12:
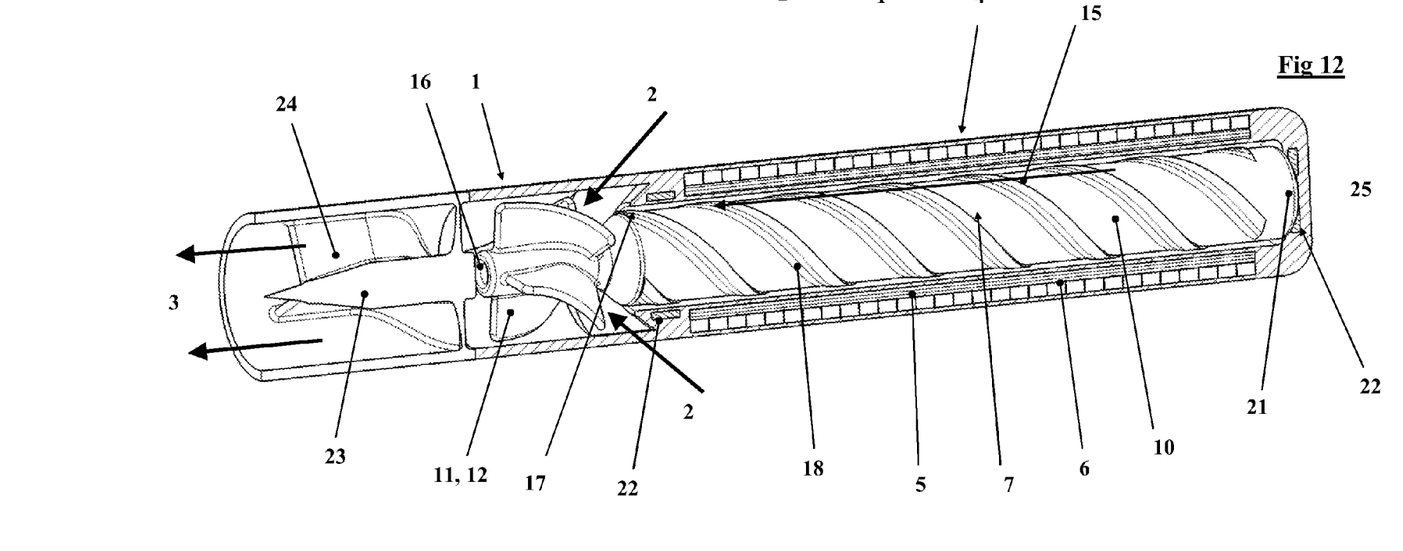
FIG. 12 is a partial cutaway view of the pump of FIG. 11.
Figure 13:
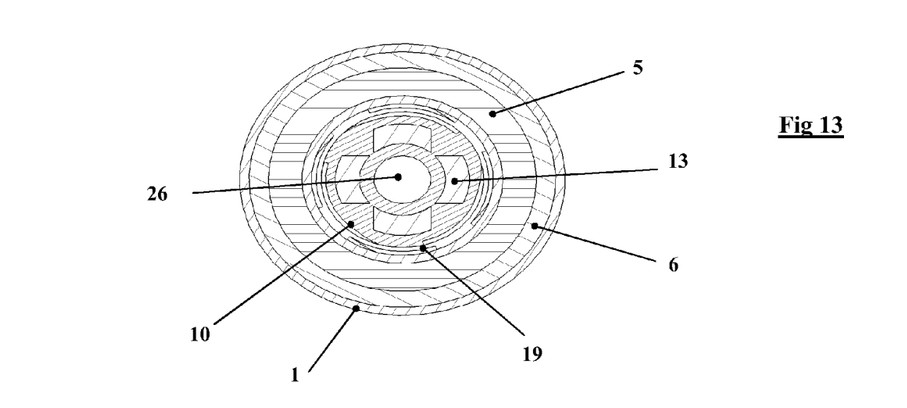
FIG. 13 is a full radial sectional view of the pump of FIG. 11.
Figure 14:
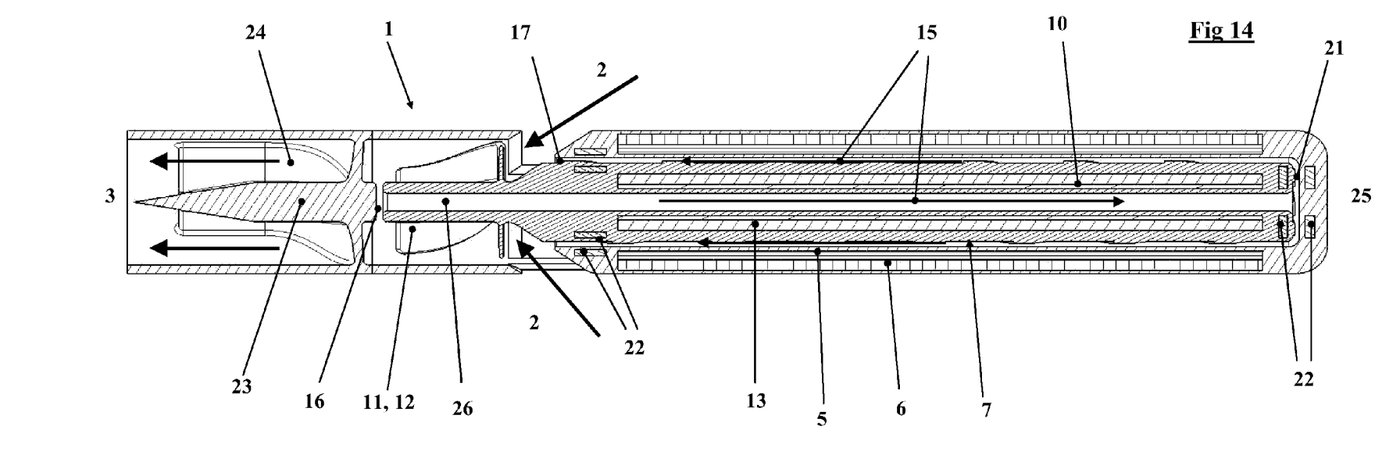
FIG. 14 is a full axial sectional view of the pump of FIG. 11.
Figure 15:
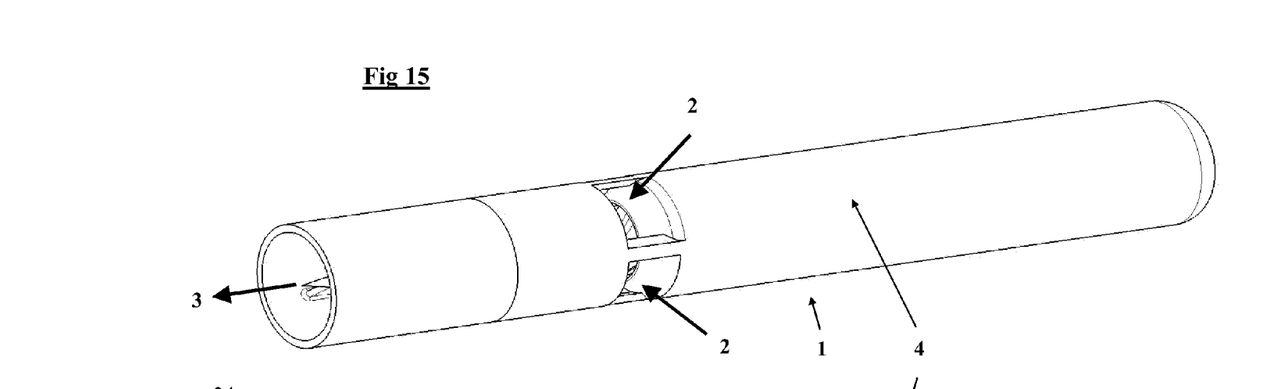
FIG. 15 is a perspective view of a fifth embodiment of a pump according to the invention.
Figure 16:
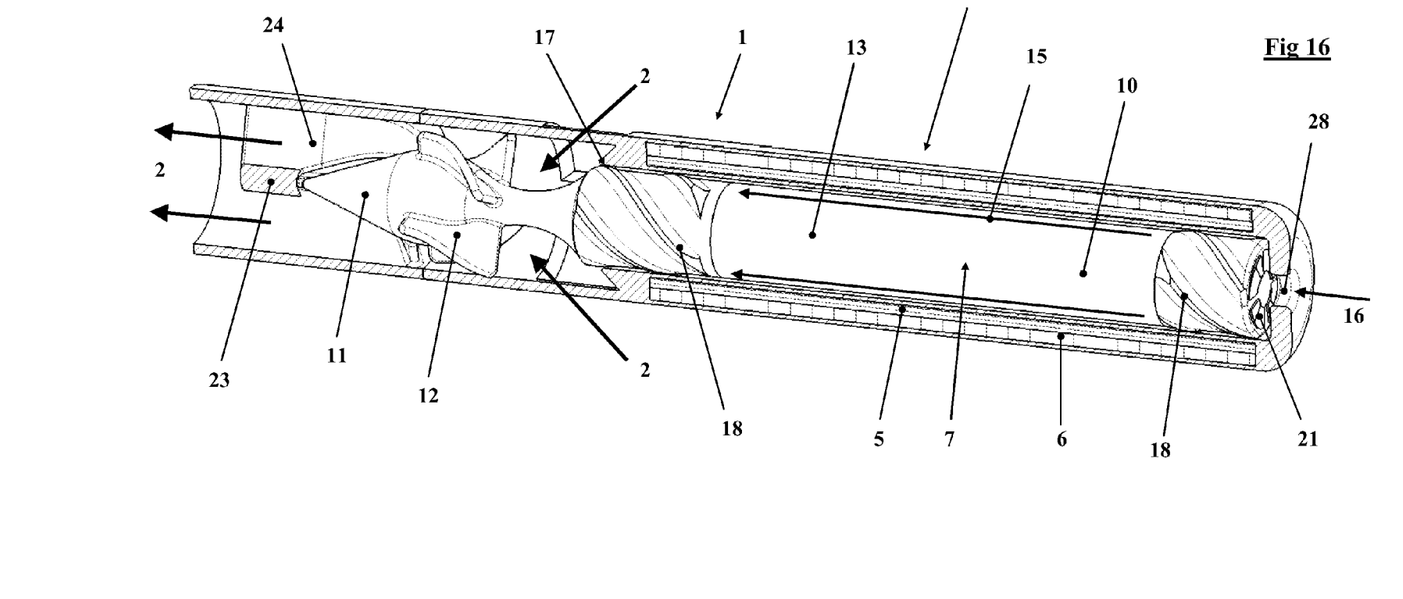
FIG. 16 is a partial cutaway view of the pump of FIG. 15.
Figure 17:
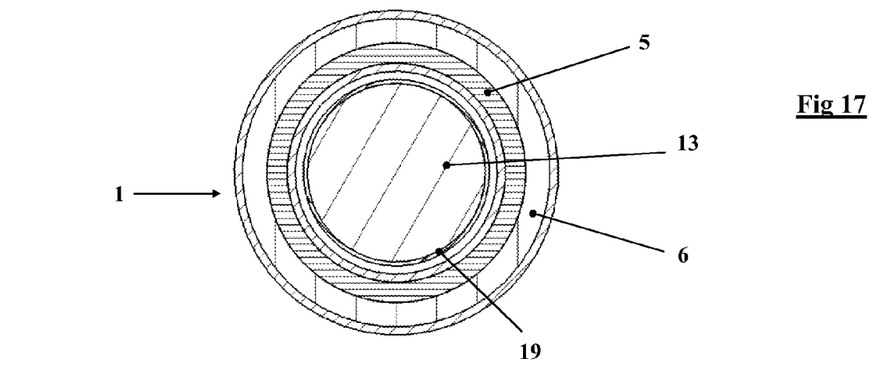
FIG. 17 is a full radial sectional view of the pump of FIG. 15.
Figure 18:
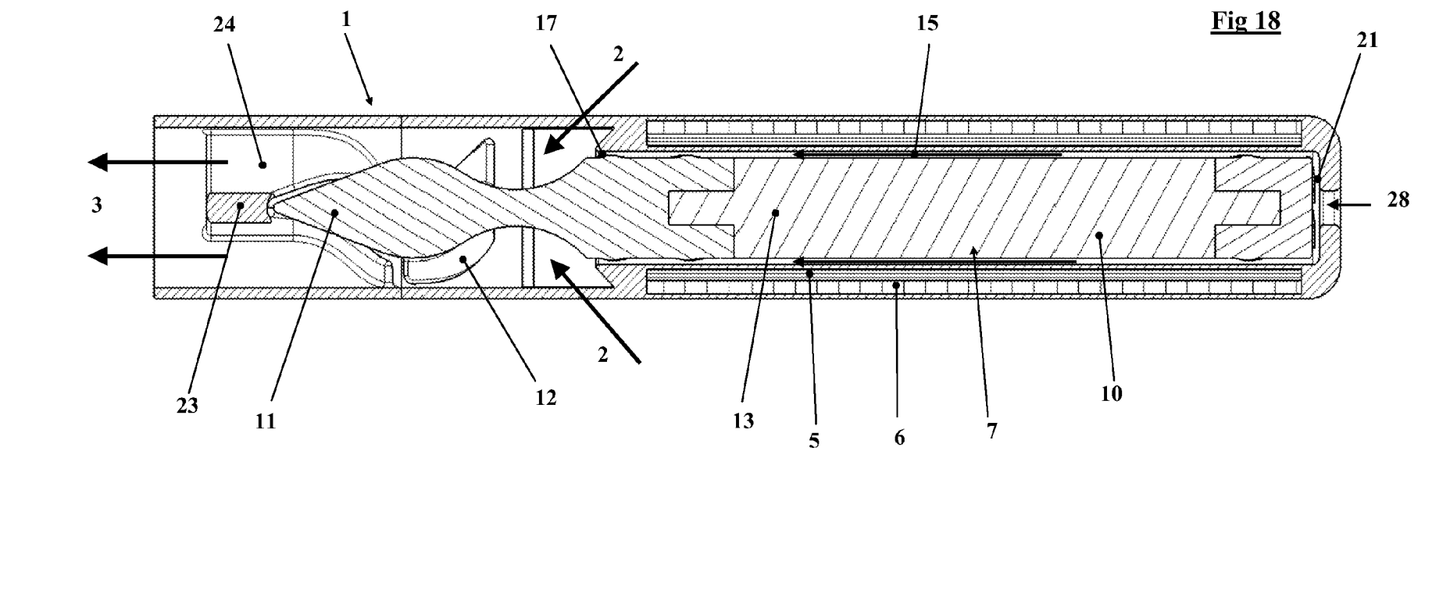
FIG. 18 is a full axial sectional view of the pump of FIG. 15.

In the embodiment of FIGS. 5 and 6, the direction of flow is reversed from the first embodiment so that inlet 2 is now at the end of the pump opposite to the impellor 12 and the outlet 3 is adjacent to it. This means that the reaction force on the rotatable element 7 is now in the opposite direction also. As a result, the widest part of the rotatable element, the pumping chamber 9, is being urged into a narrower part of the outer casing 1. Therefore whilst the pump is working, the inner rotatable element 7 is self retaining and the tail flange and bearing adjacent to the outlet of the embodiment of FIGS. 1 to 4 are not required. However, the rotatable element 7 needs to be retained so that it does not fall out of the outer casing when it is not working or if it is subject to a significant external shock loading. This problem is solved by the addition of a flow stator tube 23, comprising a series of stator blades 24 that have the dual purpose of retaining the rotatable element 7 and improving the efficiency of the pump by reducing whirl component of the flow leaving the impellor 12.

The secondary blood flow path is also reversed in direction and the inlet 16 is now at the end of the rotatable element adjacent to the impellor, and the outlet 17 is at the end of the rotatable element opposite to the impellor.

All other aspects of the pump function in a similar manner to those described with reference to the embodiment of FIGS. 1 to 4.

With reference to FIGS. 7 to 10, there is shown a third embodiment of miniature axial flow pump for blood which includes a fixed tubular outer casing 1 defining an inlet 2 at an open end of the casing 1, and one or more outlets 3 in a sidewall of the casing, with the end of the casing longitudinally spaced from the inlet 2 being a closed end 25. As in the previous embodiments it is desirable that the outer casing be of a uniform outer diameter to allow easy insertion into an artery or specific delivery device.

Integral with the outer casing 1 is a motor stator 4; the latter houses stator windings 5 and laminations 6. Rotatably held within the casing is an inner rotatable element 7 which comprises an impellor 11 and a motor rotor portion 10. The path from the inlet 2 past the impellor 11 to the outlet 3 defines the primary blood flow path 8 of the pump.

The motor rotor portion 10 further comprises rotor permanent magnets 13 which are positioned to co-operate with the motor stator 4.

In addition to the primary blood flow path, there is a defined secondary blood flow path 15 that separates the inner rotatable element 7 from the outer casing 1 in a contactless arrangement which allows the pump to be near wearless in operation.

The secondary blood flow path 15 is formed by the combination of:
a radial clearance between the motor stator portion 4 of the outer casing 1 and the motor rotor portion 10 of the inner rotatable element 7,
an axial clearance between the closed end 25 of the outer casing 1 and the adjacent end of the inner rotatable element 7, and
a central bore 26 in the inner rotatable element 7.

An inlet 16 to the secondary blood flow path 15 from the primary blood flow path 8 is defined by the extent of the clearance between the motor stator portion 4 and the motor rotor portion 10 nearmost to the impellor 11. An outlet 17 from the secondary blood flow path 15 to the primary blood flow path 8 is defined by a series of orifices 27 in the hub of impellor 11 extending from the central bore 26 outwardly towards the main blood flow path 8.

The inlet 16 for the secondary blood flow path 15 is downstream of the impellor 11 on the high pressure side of the pump, while the exit orifices 27 are upstream of the impellor 11 on the high pressure side of the pump. Thus blood in the secondary blood flow path 15 will naturally flow from a high to low pressure with this arrangement. In the embodiment illustrated, the secondary blood flow 15 is augmented by helical ribs 18 that serve dual functions both as additional pumping means for the secondary flow and as radial hydrodynamic bearings. The additional pumping is achieved by the helixes, giving an Archimedes screw pumping effect ensuring that the flow rate in the secondary path 15 is sufficient to avoid substantial risk of thrombus formation.

The hydrodynamic bearing function is accomplished by the helical ribs 18 having a radial slipper pad bearing profile when viewed in section 19. The large area covered by the helical ribs 18 ensures that the centralising loads are well spread out over the entire rotating element 9, which thereby reduces the shear stress at any one point and therefore reduces the risk of haemolysis.

In order to resist axial thrust load imparted onto the rotating element 7 by the impellor 11, a flange with inclined slipper pad bearing 20 is provided in the embodiment illustrated. There is also provided a second opposing slipper pad bearing 21. Even though this bearing 21 acts in the same direction as the axial thrust of the impellor 11, it will give improved overall system stability and provide resistance to shock loadings. Hydrodynamic bearings can be augmented by magnetic bearings 22 in order to provide a greater centralising force, particularly to resist external shock loadings.

The embodiment illustrated in FIGS. 11 to 14 of the accompanying drawings has many similarities to the third embodiment (FIGS. 7 to 10) so will be described primarily by way of its differences.

In the fourth embodiment as illustrated in FIGS. 11 to 14, the direction of flow is reversed relative to that of the third embodiment, so that inlet 2 is now in the side of the pump outer casing 1 and the outlet 3 is in the open end of the outer casing 1. As a result, the reaction force on the rotatable element 7 is reversed also. Consequently the motor portion 10 of the rotatable element 7 is being urged into the body of the outer casing 1. Therefore, whilst the pump is working the inner rotatable element is self retaining and the tail flange and bearing 20 of the third embodiment are not required. The bearing 21 on the end of the rotatable element 7 is still required and is the primary resistance to axial thrust load from the impellor. As in the first embodiment, this bearing may be augmented by magnetic bearings 22 if required.

Despite the inner rotatable element 7 being self retaining in use, it still needs to be retained so that it does not fall out of the outer casing when it is not working or if it is subject to a significant external shock loading. This problem is solved in a similar way to the second embodiment by the addition of a flow stator 23, comprising a series of stator blades 24 that has the dual purpose of retaining the rotatable element 7 and improving the efficiency of the pump by reducing whirl component of the flow leaving the impellor.

The secondary blood flow path 15 is also reversed in direction in the second embodiment and the inlet 16 is now in the clearance between the hub of the impellor 11 and the hub of the stator 23. The outlet 17 of the secondary flow path is at the extent of the clearance of between the motor portion 10 and the stator portion 4 closest to the impellor 11. As with previous embodiments, helical ribs 18 to augment the flow and provide a radial hydrodynamic bearing function may also be present in the fourth embodiment with the orientation of the ribs reversed to reflect the change in flow direction.

The embodiment illustrated in FIGS. 15 to 18 of the accompanying drawings has many similarities to the fourth embodiment (FIGS. 11 to 14) so will be described primarily by way of its differences.

In the fifth embodiment illustrated in FIGS. 15 to 18, the direction of flow is the same as in the fourth embodiment, with the inlet 2 in the side of the pump outer casing 1 and the outlet 3 in the open end of the outer casing 1. As indicated with reference to the fourth embodiment, the reaction force on the rotatable element 7 causes it to be urged into the body of the outer casing 1, thereby allowing the inner rotatable element 7 to be self retaining. The bearing 21 on the end of the rotatable element 7 is still required and is the primary resistance to axial thrust load from the impellor 11.

Magnetic bearings are not shown on the fifth embodiment but they may be added in a similar arrangement to those shown on the fourth embodiment if required.

As in the fourth embodiment, the inner rotatable element 7 is trapped in position by a flow stator 23 comprising a series of stator blades 24 that has the dual purpose of retaining the rotatable element 7 and improving the efficiency of the pump by reducing whirl component of the flow leaving the impellor.

The secondary blood flow path 15 flows between the inner rotatable element 7 and the outer casing 1 but not through a central bore as in previous embodiments. Instead blood enters the secondary flow path 15 through a small port 28 in the rear of the casing. As in the fourth embodiment, the outlet 17 of the secondary flow path is at the extent of the clearance of between the rotor portion 10 and the stator portion 4 closest to the impellor 11.

Another differentiating feature of the fifth embodiment is that the motor rotor portion 10 of the inner rotatable element 7 has a single solid magnet portion 13. The poles required for motor operation can be created by the magnetization process and this layout has the advantage of providing more magnetic material and therefore the potential for a more powerful motor. Typically the magnet 13 would be given a biocompatible coating.

Helical ribs 18 either side of the magnet 13 are arranged to drive the flow through the secondary path and provide a radial hydrodynamic bearing function to centre the rotatable element 7 during operation.

All other aspects of the pump can function in a similar manner to those described with reference to the third and fourth embodiments.

In general, the pump according to the invention is designed to provide a smooth, low shear stress blood passage in order to reduce the likelihood of haemolysis, substantially without zones in which the flow could stagnate and give a risk of thrombosis.

The invention claimed is:

1. An axial flow rotary pump suitable for implantation into the human heart or vascular system, said pump having:
   (a) an elongate tubular casing having first and second ends and an internal cylindrical surface of said casing,
   (b) an inlet for blood into said pump at said first end of said casing,
   (c) an outlet for blood from said pump, said outlet being longitudinally spaced from said inlet,
   (d) an electric motor stator provided in said casing,
   (e) an elongate tubular rotatable element having an outer surface with an outer diameter and an inner diameter, said rotatable element being arranged to fit within said casing with clearance between said outer surface and said internal cylindrical surface,
   (f) a driveable electric motor rotor portion arranged to be driven by said electric motor stator,
   (g) a primary substantially axial blood flow path extending from said inlet to said outlet and along the inside of said tubular rotatable element,
   (h) a pumping chamber having therein a rotary impeller for impelling blood along said primary flow path, wherein said pumping chamber is axially spaced from said motor rotor portion to define an axial offset spacing between said pumping chamber and said motor rotor portion and wherein said pumping chamber has an internal diameter greater than the inner diameter of said tubular rotatable element, and
   (i) a secondary blood flow path in said clearance between the outer surface of said tubular rotatable element and the inner surface of said tubular casing.

2. The pump according to claim 1, wherein the internal diameter of the pumping chamber is greater than the outer diameter of the tubular rotatable element.

3. The pump according to claim 1, wherein the casing has a substantially uniform outer diameter along at least the majority of the length thereof.

4. The pump according to claim 1, wherein at least part of the tubular rotatable element forming the blood path has a substantially uniform inner diameter along at least the majority of the length thereof.

5. The pump according to claim 1, wherein at least one of said outer surface of said tubular rotatable element and said inner surface of said casing has at least one longitudinally or helically extending groove or rib thereon.

6. The pump according to claim 1, wherein said clearance is such as to result in a hydrodynamic bearing effect.

7. The pump according to 1, which further includes at least one additional impeller within said motor rotor portion for impelling blood along said primary flow path.

8. The pump according to claim 1, wherein the inlet is at one end of the casing and the outlet is at the other end thereof.

9. The pump according to claim 1, wherein at least one of the inlet and the outlet comprises at least one aperture provided in a wall of said casing and the other thereof being an open end thereof.

10. The pump according to claim 9, which further includes a stator member for retaining said tubular rotatable element within the casing.

11. An axial flow rotary pump suitable for implantation into the human heart or vascular system, said pump comprising:
   (a) an elongate tubular casing having first and second ends and an internal cylindrical surface of said casing;
   (b) an inlet for blood into said pump at said first end of said casing;
   (c) an outlet for blood from said pump, said outlet being longitudinally spaced from said inlet;
   (d) an electric motor stator provided in said casing;
   (e) an elongate tubular rotatable element having an outer surface with an outer diameter, and an inner diameter, said rotatable element being arranged to fit within said casing with clearance between said outer surface and said internal cylindrical surface;
   (f) a driveable electric motor rotor portion arranged to be driven by said electric motor stator, the motor rotor portion having a proximal end within the tubular casing and having a distal end at said second end of the casing;
   (g) a primary substantially axial blood flow path extending from said inlet to said outlet and along the inside of said tubular rotatable element;

(h) a pumping chamber having therein a rotary impeller for impelling blood along said primary flow path, the impeller having a proximal end at said first end of said casing and a distal end within the tubular casing, wherein the distal end of the impeller is axially spaced from the proximal end of the motor rotor portion and configured to define an axial offset spacing between said pumping chamber and said motor rotor portion and wherein said pumping chamber has an internal diameter greater than the inner diameter of said tubular rotatable element; and (i) a secondary blood flow path in said clearance between the outer surface of said tubular rotatable element and the inner surface of said tubular casing.

12. The pump according to claim 11, wherein the internal diameter of the pumping chamber is greater than the outer diameter of the tubular rotatable element.

13. The pump according to claim 11, wherein the casing has a substantially uniform outer diameter along at least the majority of the length thereof.

14. The pump according to claim 11, wherein at least part of the tubular rotatable element forming the blood path has a substantially uniform inner diameter along at least the majority of the length thereof.

15. The pump according to claim 11, wherein at least one of said outer surface of said tubular rotatable element and said inner surface of said casing has at least one longitudinally or helically extending groove or rib thereon.

16. The pump according to claim 11, wherein said clearance is such as to result in a hydrodynamic bearing effect.

17. The pump according to 11, which further includes at least one additional impeller within said motor rotor portion for impelling blood along said primary flow path.

18. The pump according to claim 11, wherein the inlet is at one end of the casing and the outlet is at the other end thereof.

19. The pump according to claim 11, wherein at least one of the inlet and the outlet comprises at least one aperture provided in a wall of said casing and the other thereof being an open end thereof.

20. The pump according to claim 19, which further includes a stator member for retaining said tubular rotatable element within the casing.

21. An axial flow rotary pump suitable for implantation into the human heart or vascular system, said pump comprising:

(a) an elongate tubular casing having first and second ends and an internal cylindrical surface of said casing;

(b) an inlet for blood into said pump at said first end of said casing;

(c) an outlet for blood from said pump, said outlet being longitudinally spaced from said inlet;

(d) an electric motor stator provided in said casing;

(e) an elongate tubular rotatable element having an outer surface with an outer diameter, and an inner diameter, said rotatable element being arranged to fit within said casing with clearance between said outer surface and said internal cylindrical surface;

(f) a driveable electric motor rotor portion arranged to be driven by said electric motor stator, the motor rotor portion having a proximal end within the tubular casing and having a distal end at one of said ends of the casing;

(g) a primary substantially axial blood flow path extending from said inlet to said outlet and along the inside of said tubular rotatable element;

(h) a pumping chamber having therein a rotary impeller for impelling blood along said primary flow path, the impeller having a proximal end at one of said ends of said casing and a distal end within the tubular casing, wherein the proximal end and the distal end of the impeller are axially spaced from the proximal end of the rotor portion and configured to define an axial offset spacing between said pumping chamber and said motor rotor portion, and wherein said pumping chamber has an internal diameter greater than the inner diameter of said tubular rotatable element; and (i) a secondary blood flow path in said clearance between the outer surface of said tubular rotatable element and the inner surface of said tubular casing.

* * * * *

UNITED STATES PATENT AND TRADEMARK OFFICE
CERTIFICATE OF CORRECTION

| | |
|---|---|
| PATENT NO. | : 8,731,664 B2 |
| APPLICATION NO. | : 12/664163 |
| DATED | : May 20, 2014 |
| INVENTOR(S) | : Foster et al. |

It is certified that error appears in the above-identified patent and that said Letters Patent is hereby corrected as shown below:

In the Claims:

In Column 8, Lines 34 - 36, Claim 7 should read: --The pump according to claim 1, which further includes at least one additional impeller within said motor rotor portion for impelling blood along said primary flow path.--

In Column 9, Lines 31 - 33, Claim 17 should read: --The pump according to claim 11, which further includes at least one additional impeller within said motor rotor portion for impelling blood along said primary flow path.--

Signed and Sealed this
Ninth Day of September, 2014

Michelle K. Lee
*Deputy Director of the United States Patent and Trademark Office*